US008198026B2

(12) United States Patent
Chemeris et al.

(10) Patent No.: US 8,198,026 B2
(45) Date of Patent: Jun. 12, 2012

(54) METHOD OF DETECTING SPECIFIC FRAGMENTS OF DNA OR RNA WITH THE AID OF A REAL-TIME POLYMERASE CHAIN REACTION

(75) Inventors: Alexei Viktorovich Chemeris, g. Ufa (RU); Yury Mikhailovich Nikonorov, g. Ufa (RU); Maiya Leonidovna Romanenkova, g. Ufa (RU); Dmitry Alexeevich Chemeris, g. Ufa (RU); Ravil Rinatovich Garafutdinov, g.Meleuz (RU); Roza Azatovna Magazova, g.Ufa (RU); Grigory Vladimirovich Maleev, Moscow (RU); Vener Absatarovich Vakhitov, g. Ufa (RU); Raif Gayanovich Vasilov, Moscow (RU)

(73) Assignee: Institut Biokhimii I Genetiki Ufimskogo Nauchnogo Tsentra Ran, Moscow (RU)

( * ) Notice: Subject to any disclaimer, the term of this patent is extended or adjusted under 35 U.S.C. 154(b) by 588 days.

(21) Appl. No.: 11/553,223

(22) Filed: Oct. 26, 2006

(65) Prior Publication Data

US 2007/0117125 A1 May 24, 2007

(30) Foreign Application Priority Data

Oct. 26, 2005 (RU) .................................. 2005132940

(51) Int. Cl.
*C12Q 1/68* (2006.01)
*C12P 19/34* (2006.01)
*C07H 21/04* (2006.01)
(52) U.S. Cl. ...................... 435/6.12; 435/91.2; 536/24.3; 536/24.33
(58) Field of Classification Search .................. 435/91.2, 435/6, 6.12; 536/24.3, 24.33
See application file for complete search history.

(56) References Cited

U.S. PATENT DOCUMENTS

| | | | | |
|---|---|---|---|---|
| 7,160,996 | B1 * | 1/2007 | Cook | ........................... 536/24.3 |
| 7,273,730 | B2 * | 9/2007 | Du Breuil Lastrucci | .... 435/91.2 |
| 2002/0197611 | A1 * | 12/2002 | Chagovetz | ........................ 435/6 |
| 2007/0059690 | A1 * | 3/2007 | Islam et al. | ....................... 435/6 |

OTHER PUBLICATIONS

Bengtsson, et al., "A new minor groove binding asymmetric cyanine reporter dye for real-time PCR" Nucl. Acids Res. 2003. V. 31. e45.
Cairns et al., "Homogeneous real-time detection and quantification of nucleic acid amplification using restriction enzyme digestion" Biochem. Biophys. Res. Comm. 2004. V. 318. p. 684-690.
Higuchi et al., "Simultaneous amplification and detection of specific DNA sequences" Biotechnology 1992 V.10.P. 413-417.
Higuchi et al., "Kinetic PCR analysis: real-time monitoring of DNA amplification reactions" Biotechnology. 1993. V.11.P. 1026-1030.
Horejsh, et al., "A molecular beacon, bead-based assay for the detection of nucleic acids by flow cytometry" Nucleic Acids Res. 2005. V.33.e13.
Huang et al., "Real-time quantitative assay of telomerase activity using the duplex scorpion primer" Biotechnol. Letter 2004. V.26.P. 891-895.
Johnson et al., "A third base pair for the polymerase chain reaction: inserting isoC and isoG" Nucleic Acids Res. 2004. V.32.P. 1937-1941.
Kandimalla et al., "Cylicons as hybridization-based fluorescent primerprobes: Synthesis, properties and application in real-time PCR" Bioorg. Med. Chem. 2000. V.8.P. 1911-1916.
Lee et al., "Allelic discrimination by nick-translation PCR with fluorogenic probes" Nucl. Acids Res. 1993. V.21.P. 3761-6.
Livak et al., "Oligonucleotides with fluorescent dyes at opposite ends provide a quenched probe system useful for detecting PCR product and nucleic acid hybridization" PCR Methods Appl. 1995. V.4.P. 357-362.
Nazarenko et al., "A closed tube format for amplification and detection of DNA based on energy transfer" Nucleic Acids Res. 1997. V.25.P. 2516-2521.
Rasmussen et al., "Development of a novel quantitative real-time RT-PCR assay for the simultaneous detection of all serotypes of foot-and-mouth disease virus" Arch. Virol. 2003. V.148.P. 2005-2021.
Solinas et al., "Duplex Scorpion primers in SNP analysis and FRET applications" Nucleic Acids Res. 2001.V.29. E96.
Thelwell et al., "Mode of action and application of Scorpion primers to mutation detection" Nucleic Acids Res. 2000.V.28.P. 37523761.
Tyagi et al., "Molecular beacons: probes that fluoresce upon hybridization" Nat. Biotechnol. 1996.V.14.P. 303-308.
Tyagi et al., "Wavelength-shifting molecular beacons" Nat. Biotechnol. 2000. V.18.P. 1191-1196.
Wittwer et al., "Continuous fluorescence monitoring of rapid cycle DNA amplification" Biotechniques. 1997.V.22.P. 130-131, 134-138.
Wittwer et al., "High-resolution genotyping by amplicon melting analysis using LCGreen" Clin. Chem. 2003. V.49.P. 853-860.
Zhang et al., "A novel real-time quantitative PCR method using attached universal template probe" Nucleic Acids Res. 2003. V.31. e123.
Zhou et al., "Closed-tube genotyping with unlabeled oligonucleotide probes and a saturating DNA dye" Clin. Chem. 2004. V.50.P. 1328-1335.

* cited by examiner

*Primary Examiner* — Kenneth R. Horlick
*Assistant Examiner* — Joyce Tung
(74) *Attorney, Agent, or Firm* — Fish & Richardson P.C.

(57) ABSTRACT

Methods of amplifying specific fragments of DNA or RNA with the aid of a polymerase chain reaction in real time are disclosed. The methods include providing a first oligonucleotide primer that comprises a donor fluorescent dye and a second oligonucleotide primer that comprises an acceptor fluorescent dye; allowing the primers to anneal to a target nucleic acid at positions abutting to each other or overlapping; carrying out a polymerase chain reaction which allows for a fluorescent resonance transfer of energy between the donor dye and the acceptor dye; detecting an increase of fluorescent emission of the acceptor dye; and correlating the increase in the emission of the acceptor dye with the accumulation of the specific fragment of DNA or RNA. In one embodiment, the primers comprise a fluorescent dye and a universal quencher.

4 Claims, 3 Drawing Sheets

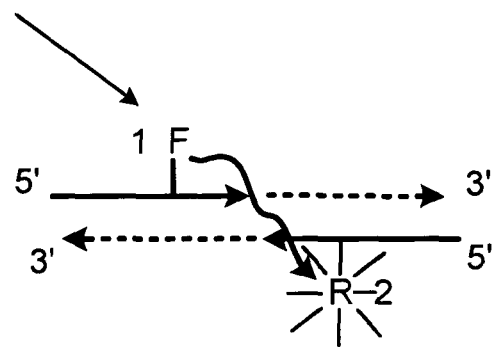
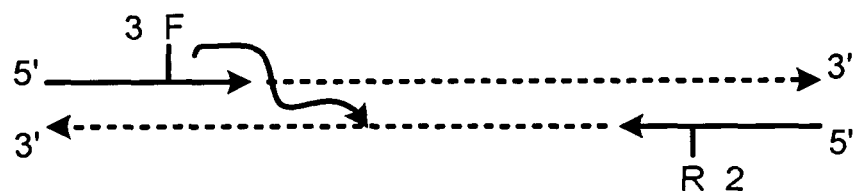
FIG. 3B
FIG. 3A
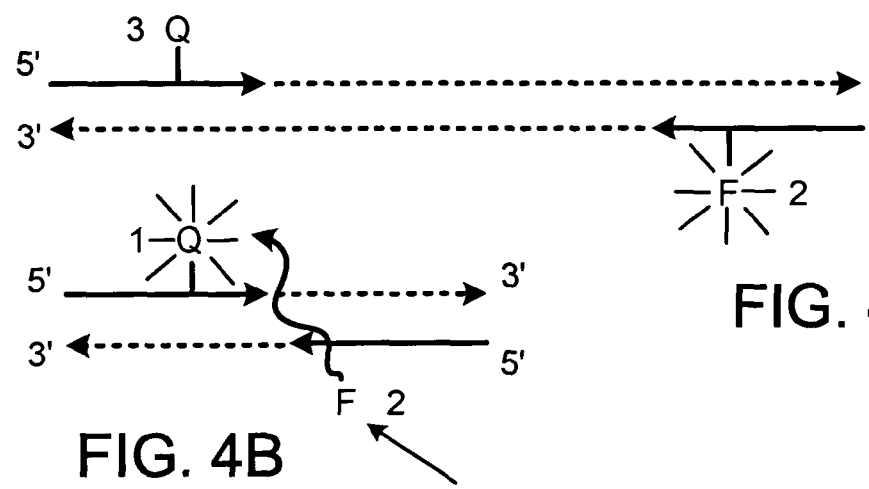
FIG. 4A
FIG. 4B

METHOD OF DETECTING SPECIFIC FRAGMENTS OF DNA OR RNA WITH THE AID OF A REAL-TIME POLYMERASE CHAIN REACTION

TECHNICAL FIELD

The invention relates to molecular biology and biotechnology and is related to an analysis of DNA and/or RNA molecules. It may be used during the conduction of DNA diagnostics in medicine, veterinary medicine, sanitary-epidemiological research, criminalistics, food industry for detection of pathogens of dangerous infections, including possible bioterrorist attacks, identification of criminals, detection of food products made from genetically modified organisms, determination of the quality of raw materials, etc.

BACKGROUND

Existing methods of DNA diagnostics are based primarily on the amplification of specific fragments of DNA or RNA with the aid of a polymerase chain reaction (PCR) and modifications thereof. In recent times the so-called PCR in real time, when detection of the desired product is conducted directly during amplification with the aid of special DNA thermocyclers provided with an optical module, has been the most widely used method. One of the important advantages of such an approach is the absence of the necessity of carrying out the step of electrophoretic separation of the reaction products, which step presumes the opening of test tubes and manipulation of their content in air, as a result of which the working zone of the rooms may be contaminated with the PCR products—amplicons, generally presented by billions of copies. This may result in the obtainment during subsequent analyses of false-positive results, which may occur since the new reaction mixtures may be initially contaminated in an aerosol manner with amplicons formed during preceding positive reactions and circulating in the air medium. In addition to this, the possibility of a procedure without electrophoretic analysis significantly reduces the time necessary for the whole procedure. Another important advantage is the possibility to obtain, with the aid of real-time PCR, an exact quantitative determination of the number of copies of one or another target, for example, the content of genetically modified ingredients or any other admixtures in raw material or food products.

SUMMARY

The object of the invention is to significantly simplify, accelerate and reduce the cost of obtaining the results of real-time PCR, while maintaining high specificity of the reaction. The present invention is based, in part, on the discovery that high specific detection of desired products of PCR can be carried out in a special DNA amplifier provided with an optical module, wherein in the process of amplification itself, the increase in the amount of desired products is detected according to, or relative to, an increasing intensity of the emission of an acceptor dye after the transfer of fluorescent resonance energy thereto from a donor dye or, in another variant, according to, or relative to, a decreasing emission of the fluorescent dye as a result of the effect of a quenching. The dyes are separately included in the structure of quite ordinary (if their modification in the form of fluorescent dyes is not taken into account), deprived of a secondary structure, forward and reverse primers. On the other hand, either hybridization probes of the TaqMan or Beacon or others, or complex primer constructions of the Sunrise, Scorpion or Cyclicon type, which have a complex secondary structure or intercalating dyes characterized by low specificity are used for this purpose in the real-time PCR methods used at the present time.

In one aspect, the invention features a method of amplifying specific fragments of DNA or RNA with the aid of a polymerase chain reaction in real time, the method comprising: (a) providing a first oligonucleotide primer that comprises a donor fluorescent dye and a second oligonucleotide primer that comprises an acceptor fluorescent dye; (b) allowing the primers to anneal to a target nucleic acid at positions abutting to each other (or overlapping); (c) carrying out a polymerase chain reaction which allows for a fluorescent resonant transfer of energy between the donor dye and the acceptor dye; (d) detecting an increase of fluorescent emission of the acceptor dye; and (e) correlating the increase in the emission of the acceptor dye with the accumulation of the specific fragment of DNA or RNA.

Embodiments can include one or more of the following elements.

The first oligonucleotide primer is a forward primer, and the second oligonucleotide primer is a reverse primer. The use of hybridization probes is not necessary in the featured methods. The oligonucleotide primers that are used do not form secondary structures.

In another aspect, the invention features a method of amplifying specific fragments of DNA or RNA with the aid of a polymerase chain reaction in real time, the method comprising: (a) providing a first oligonucleotide primer that comprises a fluorescent dye and a second oligonucleotide primer that comprises a universal quencher; (b) allowing the primers to anneal to a target nucleic acid at positions abutting to each other; (c) carrying out a polymerase chain reaction which allows for a quenching effect between the fluorescent dye and the universal quencher; (d) detecting a reduction in emission of the fluorescent dye; and (e) correlating the decrease in the emission of the fluorescent dye with the accumulation of the specific fragment of DNA or RNA.

Embodiments can include one or more of the following features.

The first oligonucleotide primer is a forward primer, and the second oligonucleotide primer is a reverse primer. The use of hybridization probes is not necessary in the featured methods. The oligonucleotide primers that are used do not form secondary structures.

All publications, patent applications, patents, and other references mentioned herein are incorporated by reference in their entirety. In addition, the materials, methods, and examples are illustrative only and not intended to be limiting. Other features and advantages of the disclosure will be apparent from the following detailed description, the drawings, and the claims.

BRIEF DESCRIPTION OF THE DRAWINGS

FIG. 3A is a diagram depicting a scheme of real-time PCR without the transfer of fluorescent resonance energy between the donor (F) and acceptor (R) dyes.

FIG. 3B is a diagram depicting a scheme of real-time PCR with the transfer of fluorescent resonance energy between the donor (F) and acceptor (R) dyes. The transfer of energy is shown by the wavy arrow.

FIG. 4A is a diagram depicting a scheme of real-time PCR without quenching of the emission of the fluorescent dye (F) by the universal quencher (Q).

FIG. 4B is a diagram depicting a scheme of real-time PCR with quenching of the emission of the fluorescent dye (F) by the universal quencher (Q).

DETAILED DESCRIPTION

Currently-Available Real-Time PCR Methods

Figure 1:
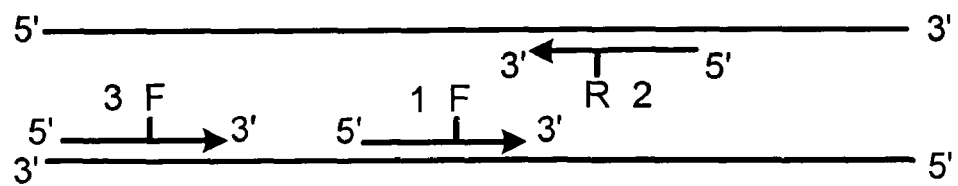
FIG. 1 is a diagram depicting a scheme of positioning of forward (1 and 3) and reverse (2) primers in a variant of real-time PCR with the transfer of fluorescent resonance energy between donor (F) and acceptor (R) dyes.

At the present time, there are quite a few schemes for detecting desired products by real-time PCR, which may be generally divided into high specific and low specific. The low specific techniques should include those which make it possible to detect only the appearance of new DNA fragments as such, in the reaction mixture, independent of their nucleotide sequence, through the emission of intercalating dyes, such as ethidium bromide [Higuchi et al., Biotechnology. 1992. V.10.P. 413-417; Higuchi et al., Biotechnology. 1993. V.11.P. 1026-1030], SYBR Green I [Wittwer et al., Biotechniques. 1997. V.22.P. 130-131, 134-138], BEBO [Bengtsson et al., Nucl. Acids Res. 2003. V. 31. e45], LCGreen [Wittwer et al., Clin. Chem. 2003. V.49.P.853-860; Zhou et al., Clin. Chem. 2004. V.50.P. 1328-1335], which in a complex with DNA emit significantly stronger signals as compared with their background fluorescence. A possible advantage of these methods is that they are inexpensive.

The group of low specific methods should also include variants of real-time PCR that are based on a change of the fluorescence of one of the primers, which occurs during the amplification and operation of double-stranded DNA fragments. The reason for their low or at least reduced specificity is that a change of the emission in this case does not depend on the second primer, or more exactly, on the place where it is annealed. That is, as a result of the possible nonspecific annealing (at such a distance from each other that the building of new DNA fragments will still be possible) of both primers or of only one marked primer as the "forward" and "reverse" right away in two places, amplification of the already non-specific DNA fragment in this case will take place anyway, but in the course of the increase or reduction in the fluorescence it will not be possible to determine that it is not specific. So, for example, variants of real-time PCR (a) with the positioning in one of the primers of a dye and quencher, which in the process of amplification should spatially separate under the action of thermally stable restriction endonuclease, since at first a site of recognition of this enzyme is present in the primer sequence [Cairns et al., Biochem. Biophys. Res. Comm. 2004. V. 318. P. 684-690], or (b) with the presence of fluorochrome and a closely positioned thereto unnatural nitrogenous base isoC in the structure of the primer, which in the process of amplification results in the introduction of a complementary thereto IsoG carrying a universal quencher into another DNA chain [Johnson et al., Nucleic Acids Res. 2004. V.32.P. 1937-1941], cannot be regarded as high specific methods, in spite of the fact that in case (a) of real-time PCR utilizing a modified primer with a restriction site this results in an increase of fluorescence, and in case (b)—to a decrease thereof. An additional disadvantage of some low specific methods is the complexity of the primer structures of the Sunrise [Nazarenko et al., Nucleic Acids Res. 1997. V.25.P. 2516-2521], Scorpion [Thelwell et al., Nucleic Acids Res. 2000.V.28.P. 3752-3761; Solinas et al., Nucleic Acids Res. 2001.V.29. E96; Huang et al., Biotechnol. Lett. 2004. V.26.P. 891-895], Cyclicon [Kandimalla, Agrawal, Bioorg. Med. Chem. 2000. V.8.P.1911-1916] and other types. Further, there are additional nucleotide sequences contained in such a primer in addition to a region annealing to the desired sequence, which may also have a significant affect on the specificity of the annealing.

One proposed real-time PCR method, designed for use with a hybridization universal UT probe [Zhang et al., Nucleic Acids Res. 2003. V.31.e123], has an advantage that the probe may in fact be of just one type for almost all of the cases, which significantly reduces expenses related to real-time PCR, but the place for annealing the probe is positioned on one of the specially lengthened for this purpose primers and only in this respect the method should be recognized as being low specific. A hybridization probe has also been used by Rasmussen et al., Arch. Virol. 2003. V.148. P.2005-2021. The authors called their method PriProET, but positioned the donor and acceptor dyes at a large distance from each other and made the size of the amplicon very large, which did not result in the advantages of the instant still high specific approach.

The methods of detection of the desired product by real-time PCR, which are based on the use of a hybridization probe, should be considered to be high specific in view of the fact that in addition to the two specifically annealing primers, such systems also have a probe, marked in a corresponding manner, that confirms by its hybridization with the amplicon the identity of the product with the expected product. Among such probes, the most widely spread is the method of so-called TaqMan detection, which is based on the use of 5'-exo-nuclease activity of the Taq polymerase, under the effect of which destruction of the hybridization probe annealed to the amplicon and detachment of the fluorochrome, which begins emission, take place, while when it is in the structure of the probe together with the quencher its emission is extinguished [Lee et al., Nucl. Acids Res. 1993. V.21.P. 3761-6; Livak et al., PCR Methods Appl. 1995. V.4.P. 357-362]. Another high specific method of real-time PCR is based on the use of Molecular Beacon, which is an oligonucleotide hairpin with dye and quencher positioned on the 5'- and 3'-ends [Tyagi, Kramer, Nat. Biotechnol. 1996.V.14.P.303-308; Tyagi et al., Nat. Biotechnol. 2000. V.18.P.1191-1196, Horejsh et al., Nucleic Acids Res. 2005. V.33.e13]. When a region of single-stranded DNA, that is complementary to this probe, is formed in the process of amplification, the hairpin opens and anneals, which is accompanied by spatial distancing of the dye from the quencher, resulting in an increase of fluorescence.

The main drawback of all of these real-time PCR systems is their complexity and the necessity to use a greater number of components than are present in an ordinary PCR, wherein in addition to the initial DNA, DNA polymerase and deoxy-nucleotide triphosphates, usually only two primers are sufficient for diagnostic purposes. The use of hybridization probes, carrying therein two, or sometimes three modifications (significantly increasing their cost), also presumes the presence of a specific region, serving as a target for such a probe, between the places of annealing of the primers, which also inevitably results in that the size of the amplicon increases and usually exceeds 60-70 bp and even more.

Presently Featured Real-Time PCR Methods

The object of the present invention is to significantly simplify, accelerate and reduce the cost of obtaining the results of real-time PCR, while maintaining high specificity of the reaction.

The invention is based, inter alia, on high specific detection of desired products of PCR carried out in a special DNA thermocycler provided with an optical module, wherein in the process of the amplification itself, the increase in the amount of desired products is detected according to, e.g., relative to, an increasing intensity of the emission of an acceptor dye after the transfer of fluorescent resonance energy thereto from a donor dye or, in another variant, according to, e.g., relative to, a decreasing emission of the fluorescent dye as a result of the effect of a quencher. The dyes are separately included in the structure of quite ordinary (if their modification in the form of fluorescent dyes is not taken into account), deprived of a secondary structure, forward and reverse primers. On the other hand, hybridization probes of the TaqMan or Beacon or other types, or complex primer constructions of the Sunrise, Scorpion or Cyclicon type, which have a complex secondary structure or intercalating dyes characterized by very low specificity are used for this purpose in the real-time PCR methods used at the present time.

The main distinction of the featured methods is that generally there is no need of any additional structures in the form of hybridization probes, which make this process significantly more expensive and somewhat slower. In one variant of the methods disclosed herein, the standard 25 cycles are accomplished in less than about 25 min, since the size of the amplicon is only about 35-50 bp in view of the fact that the areas of the nucleotide sequences of the DNA or RNA fragments to be detected, which are selected as places for annealing the forward and the reverse primers, are located abutting to each other or may even partially overlap. The high specificity of the real-time PCR method disclosed herein, also called "UFA" (Universal Fluorescent Amplification) is provided in that the donor dye and the acceptor dye or, in another variant, the dye and quencher, are included in the structure of different (forward and reverse) primers. On one hand this eliminates possible non-specific amplification (or more precisely, its detection) only from one of the primers, and on the other hand—requires annealing of both primers in direct proximity to each other, which in accordance with the theory of probability is a virtually improbable event for an area that is not selected as the region to be detected.

The featured methods of amplification UFA with the aid of a polymerase chain reaction of specific fragments of DNA or RNA together with their detection in the real time are illustrated by the following examples that are not meant to limit the scope and spirit of the invention.

Example 1

Selection of Oligonucleotide Primers

Figure 2:
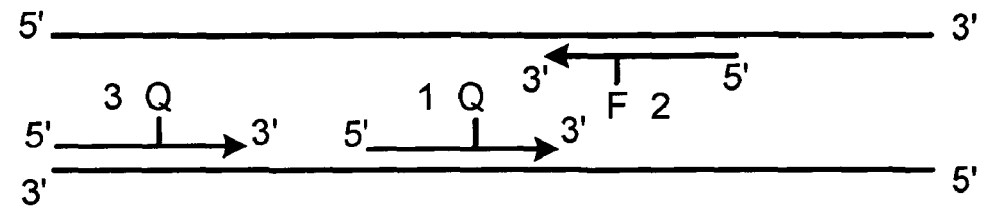
FIG. 2 is a diagram depicting a scheme of positioning of forward (1 and 3) and reverse (2) primers in a variant of real-time PCR with quenching of the emission of the fluorescent dye (F) by the universal quencher (Q).

The selection of oligonucleotide primers is carried out with the expectation that they would provide specificity of the reaction and limit the size of the fragment of nucleotide sequence of the DNA (or RNA) to a size of 35-50 pairs of nucleotides (or nucleotides) respectively. The following circumstance should be taken into account during the selection of the primers—that in the process of synthesis of the oligonucleotide primers (or following synthesis) they could be marked with corresponding fluorescent dyes and quenchers, characterized by suitable wavelengths of excitation and emission and thus composing either a donor/acceptor pair (FIG. 1) or a dye/quencher pair (FIG. 2) and as a result of amplification be spaced from each other in a desired double-stranded product at a distance where the transfer of fluorescent resonance energy (FIG. 3A and FIG. 3B) or quenching (FIG. 4A and FIG. 4B) is effectively detected. Primers for negative-positive control were selected, taking into account that the distance between (a) the donor dye and the acceptor dye or (b) dye and quencher would not make it possible in the first case (a) to carry out transfer of the fluorescent resonance energy, and in the second (b)—the effect of quenching would not be present, but wherein the corresponding real-time PCR product would be produced in both cases.

Example 2

The Conduction of Preliminary DNA Amplification in Order to Determine the Melting Temperature of a Desired Product A reaction mixture with a volume of 25 μL comprises a buffer (40 mM Tris-HCl pH 8.0, 2.5 mM $MgCl_2$, 25 mM KCl); 20 fMol DNA; 1 unit of activity Taq DNA polymerase; 0.5 pMol of each of two primers, each marked with its fluorochrome (with a donor and acceptor or dye and quencher) and a corresponding amount of distilled water. Real-time PCR was conducted in a DNA thermocycler of the iCycler iQ model (Bio-Rad Laboratories, US) under the following conditions: denaturation of double-stranded DNA in the first cycle was carried out at 95° C. for 30 sec, then the primers were annealed and lengthened—at 45° C., 10 sec with registration of the fluorescence at the end of this stage, denaturation of the desired product—at 90° C., 10 sec, number of cycles—25. Control of the production of the desired product was conducted, when it was present in the form of a double-stranded molecule, by registering an increase of the emission of the acceptor dye after its excitation with the fluorescent resonant energy of the donor dye or, in another variant—a decrease of the emission of the dye as a result of the quenching effect, which are present at this stage. The annealing temperature of the primers was varied somewhat in different experiments depending on the GC composition of the used oligonucleotides. Determination of the melting temperature of the desired product of DNA amplification was carried out in the same DNA thermocycler as provided for by the corresponding protocol of the program accompanying the device. After completion of the amplification step, detection of the temperature of transition of the amplicon from the double-stranded state to the single-stranded was found by establishing the relationship of the negative value of the first derivative of fluorescence in respect to temperature, thus obtaining a differential curve of melting and experimentally determining the melting temperature of the desired product. This information is necessary for the selection of a temperature that is sufficient for sure denaturation of amplicons instead of the classical 95° C., since if the sufficient temperature is lower than 95° C., the time for the whole amplification procedure is reduced (in addition to other advantages). Taking into account that the average rate of heating and cooling the reaction blocks in DNA thermocyclers of different models usually varies from 2 to 3° C. per second, from 12 to 15 seconds may be saved in each cycle. Due to this, with a larger number of cycles, the working capacity of the enzyme is lengthened in view of the reduction of the time for which it is present at temperatures above the optimum, thus on the whole providing more reliable amplification.

Example 3

Preparation of cDNA

In order to amplify RNA comprising material with the aid of real-time PCR with an enzyme of reverse transcriptase (real-time RT-PCR), the step of building a complementary DNA according to the RNA matrix with the aid of this enzyme is necessary. Preliminarily, 0.5 μg of RNA and 0.001 $A_{260}$ units of oligonucleotide 2, serving here as a primer, were mixed in a microcentrifuge tube. The mixture was heated to 85° C. and was allowed to slowly cool to 30° C. A reverse transcription reaction was carried out at 42° C. during 10 min in a reaction volume of 20 μL of the following composition—50 mM Tris-HCl pH 8.3, 10 mM $MgCl_2$, 10 mM DTT, 0.5 mM spermidine, 0.5 mM of each of dNTP and 5 units of activity of AMV-revertase.

Example 4

Carrying Out Real-Time PCR or Real-Time RT-PCR

PCR was carried out in 25 μL of a reaction mixture comprising a buffer (40 mM Tris-HCl pH 8.0, 2.5 mM $MgCl_2$, 25 mM KCl); 20 fMol DNA; 1 unit of activity Taq DNA polymerase; 0.5 pMol of each of 2 primers marked each with its own fluorochrome (donor and acceptor or dye and quencher) and a corresponding amount of distilled water. Real-time PCR was carried out in a DNA thermocycler of the iCycler iQ model under the following conditions: denaturation of a double-stranded DNA in the first cycle was conducted at 95° C. for 30 sec, followed by annealing the primers and their lengthening—at 45° C., 10 sec with registration of the fluorescence at the end of this step, denaturation of the desired product—at 80° C., 10 sec, the number of cycles—25.

Figure 5:
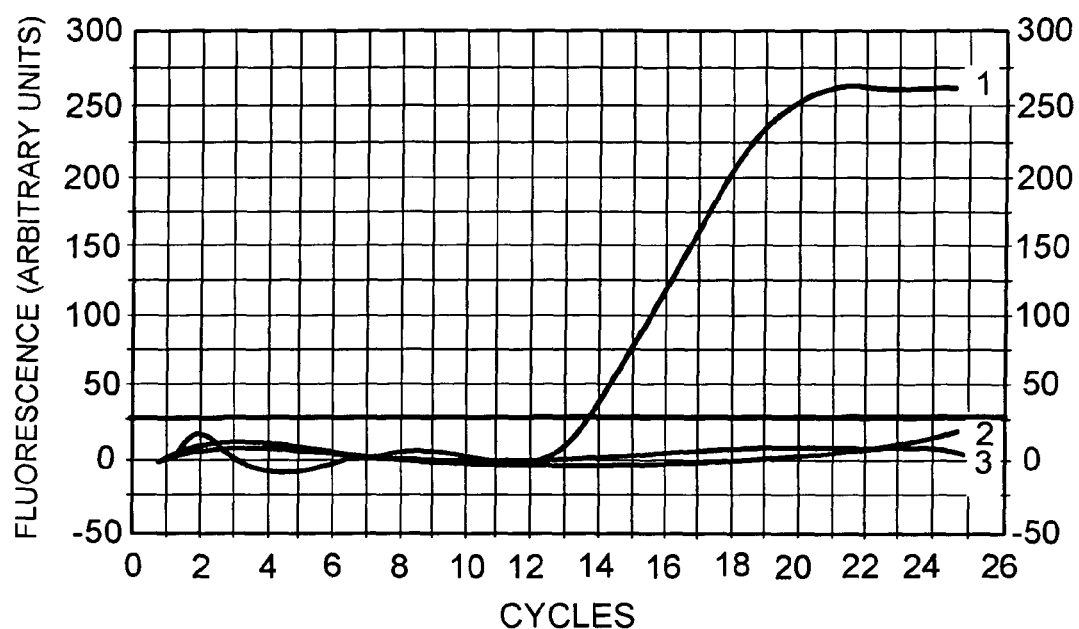
FIG. 5 is a graph depicting curves of the increase of fluorescence in the variant of real-time PCR with the transfer of fluorescent resonance energy between the donor and acceptor dyes. Curve 1 represents reaction with primers 1 and 2; curve 2 represents reaction with primers 3 and 2; curve 3 represents a negative control (reaction without matrix DNA).

Denaturation of the desired product at a reduced temperature (80° C.) for a brief period of time (10 sec) made it possible to reduce the duration of the reaction and reduce the time during which the DNA polymerase is in the critical temperature zone, since there is no necessity to heat the desired product to 95° C., because, as was determined in example 2, it denatures at a lower temperature (75° C.). The annealing temperature of the primers and also the melting temperature of the desired products varied somewhat in different experiments depending on the GC composition of the used oligonucleotides. The second variant of real-time PCR with primers marked in one case by a donor dye and in the second by a quencher was conducted in a similar manner. As control, PCR was conducted without the addition of the studied DNA (or cDNA), and also with the addition of DNA that does not comprise a region complementary to the used oligonucleotides. For additional negative-positive control, the region of the nucleotide sequence that was intended to be the location for annealing primer 3, was positioned at a significant distance from the annealing point of primer 2, and at which distance the fluorescent resonance energy is not transmitted and the effect of quenching is also absent (FIGS. 1-4). Curves of an increase of the fluorescence of the desired product, limited by primers 1 and 2, and the absence of the fluorescence under control conditions are seen in FIG. 5.

Example 5

Electrophoretic Control of Real-Time PCR Products (Optional)

Figure 6:
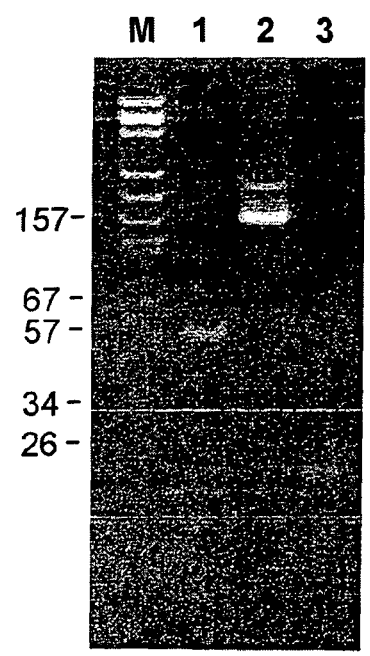
FIG. 6 is a photograph depicting electrophoretic analysis of real-time PCR products with the transfer of fluorescent resonance energy between the donor and acceptor dyes. Lane M represents marker DNA; lane 1 represents reaction with primers 1 and 2; lane 2 represents reaction with primers 3 and 2; lane 3 represents negative control (without a matrix DNA, free primers are evident).

Electrophoretic control (optional element of the disclosed methods) of the real-time PCR products was conducted with the purpose of visually detecting the desired product. Separation of the real-time PCR products was carried out in an 8% polyacrylamide gel in a tris-acetate buffer pH 7.8 in undenatured conditions at a voltage gradient of 4V per cm of gel length in a vertical type device during 4 hours. After completion of electrophoresis, the gel was stained with ethidium bromide and photographed in a photo-documentary system—Gel Camera System (UVP, Inc., US). As seen from FIG. 6, the desired product, registered during the real-time PCR, has the expected size of 42 bp, while the negative-positive control in the form of a fragment of 110 bp size did not show a change of the fluorescence signal during the real-time PCR, but if stained with ethidium bromide was quite evident. In view of the presence of two fluorochromes in the composition of the amplicons, their mobility is somewhat less than it was in the case of unmodified fragments of DNA of similar size.

A number of embodiments of the invention have been described. Nevertheless, it will be understood that various modifications may be made without departing from the spirit and scope of the invention. Accordingly, other embodiments are within the scope of the following claims.

The invention claimed is:

1. A method of amplifying specific fragments of a target DNA or RNA with the aid of a polymerase chain reaction in real time, the method comprising:
   (a) providing a first oligonucleotide primer that comprises a donor fluorescent dye and a second oligonucleotide primer that comprises an acceptor fluorescent dye, wherein the first and second oligonucleotide primers are designed to anneal to partially overlapping portions of a target nucleic acid, wherein such overlap is not more than one nucleotide;
   (b) allowing the primers to anneal to the target nucleic acid at partially overlapping positions;
   (c) carrying out a polymerase chain reaction which allows for a fluorescent resonance transfer of energy between the donor dye and the acceptor dye;
   (d) detecting an increase of fluorescent emission of the acceptor dye; and
   (e) correlating the increase in the emission of the acceptor dye with the accumulation of the specific fragment of DNA or RNA.

2. The method of claim 1, wherein the first oligonucleotide primer is a forward primer, and the second oligonucleotide primer is a reverse primer.

3. A method of amplifying specific fragments of a target DNA or RNA with the aid of a polymerase chain reaction in real time, the method comprising:
   (a) providing a first oligonucleotide primer that comprises a fluorescent dye and a second oligonucleotide primer that comprises a universal quencher, wherein the first and second oligonucleotide primers are designed to anneal to partially overlapping portions of a target nucleic acid, wherein such overlap is not more than one nucleotide;
   (b) allowing the primers to anneal to the target nucleic acid at partially overlapping positions;

(c) carrying out a polymerase chain reaction which allows for a quenching effect between the fluorescent dye and the universal quencher;
(d) detecting a reduction in emission of the fluorescent dye; and
(e) correlating the decrease in the emission of the fluorescent dye with the accumulation of the specific fragment of DNA or RNA.

4. The method of claim 3, wherein the first oligonucleotide primer is a forward primer, and the second oligonucleotide primer is a reverse primer.

* * * * *